(12) United States Patent
Everett et al.

(10) Patent No.: US 6,459,748 B1
(45) Date of Patent: Oct. 1, 2002

(54) FLOATING ULTRASONIC TESTING END EFFECTOR FOR A ROBOTIC ARM

(75) Inventors: James W. Everett, New Stanton, PA (US); James M. Adamski, Cecil, PA (US); Patrick M. Minogue, Pittsburgh, PA (US); Paul J. Boone, Bethel Park, PA (US)

(73) Assignee: Westinghouse Electric Company LLC, Pittsburgh, PA (US)

( * ) Notice: Subject to any disclaimer, the term of this patent is extended or adjusted under 35 U.S.C. 154(b) by 0 days.

(21) Appl. No.: 09/435,548

(22) Filed: Nov. 8, 1999

(51) Int. Cl.[7] .......................................... G21C 17/003
(52) U.S. Cl. ..................... 376/249; 376/245; 376/248; 376/252; 73/627; 73/631; 73/632; 73/634; 128/660.1; 128/4
(58) Field of Search ................. 376/245, 252, 376/248, 249; 73/627, 634, 632, 631; 128/660.1

(56) References Cited

U.S. PATENT DOCUMENTS

| | | | | |
|---|---|---|---|---|
| 4,196,049 A | | 4/1980 | Burns et al. ............... 176/19 R |
| 4,526,037 A | * | 7/1985 | Wentzell et al. .............. 73/640 |
| 4,643,029 A | * | 2/1987 | Klinvex ........................ 73/632 |
| 4,686,078 A | * | 8/1987 | Zwart, Jr. .................... 376/249 |
| 4,762,455 A | * | 8/1988 | Coughlan et al. ............... 414/4 |
| 4,785,819 A | * | 11/1988 | Pearce ..................... 128/660.1 |
| 4,805,477 A | * | 2/1989 | Akeel .......................... 74/479 |
| 4,868,798 A | * | 9/1989 | Fasnacht, Jr. et al. ....... 367/104 |
| 4,901,578 A | * | 2/1990 | Brill, III ...................... 73/623 |
| 4,966,746 A | * | 10/1990 | Richardson et al. ........ 376/249 |
| 5,061,176 A | * | 10/1991 | Zafred et al. ................. 432/5 |
| 5,156,803 A | * | 10/1992 | Engding et al. ............ 376/249 |
| 5,265,667 A | * | 11/1993 | Lester, II et al. .......... 165/11.2 |
| 5,327,079 A | * | 7/1994 | Haller et al. ................. 324/219 |
| 5,329,194 A | * | 7/1994 | Dow et al. ..................... 310/17 |
| 5,355,063 A | | 10/1994 | Boone et al. ............ 318/568.1 |
| 5,467,813 A | * | 11/1995 | Vermaat ..................... 165/11.2 |
| 5,586,155 A | * | 12/1996 | Erbes et al. ................ 376/249 |
| 5,611,948 A | * | 3/1997 | Hawkins ................. 219/121.63 |
| 5,771,266 A | | 6/1998 | Fabris ......................... 376/287 |
| 5,930,316 A | * | 7/1999 | Kowdley et al. ............ 376/249 |
| 6,222,897 B1 | * | 4/2001 | Hatley et al. ................ 376/245 |
| 6,285,919 B1 | * | 9/2001 | Randolph et al. ........... 700/254 |

\* cited by examiner

*Primary Examiner*—Charles T. Jordan
*Assistant Examiner*—John A. Richardson

(57) ABSTRACT

An end effector for supporting an ultrasonic testing probe on a robot arm having a robot mounting bracket for use in a nuclear reactor pressure vessel. The end effector has a wrist assembly with a rotatable wrist axle. The wrist assembly is coupled to the robot mounting bracket and a probe assembly is coupled to the wrist shaft. The ultrasonic testing probe is floatably disposed within the probe assembly.

21 Claims, 6 Drawing Sheets

FLOATING ULTRASONIC TESTING END EFFECTOR FOR A ROBOTIC ARM

BACKGROUND OF THE INVENTION

1. Field of the Invention

This invention generally concerns a robotic arm end effector, and, more specifically, a robotic arm end effector which provides a floating ultrasonic test probe that can be used to test baffle bolts installed on a nuclear reactor's pressure vessel baffle. This invention further concerns a robotic arm end effector having a portion of the end effector releasably coupled to the robotic arm.

2. Background Information

Because of the radiation hazard present within the pressurized water vessel of a nuclear reactor, maintenance and testing of components within the pressurized water vessel are typically performed by remote service devices, such as robotic arms. Such a service device typically includes a robotic arm which can generally access any point within the pressure vessel. The robotic arm will be fitted with an end effector capable of performing specific maintenance or testing tasks.

One task performed remotely is the underwater testing of baffle bolts. The pressurized water vessel of a nuclear reactor houses a baffle constructed of multiple flat plates. The flat plates of the baffle are bolted together and the bolts, which are recessed in the baffle, are held in place by a lock bar welded across the bolt head and to the baffle. While the reactor is in use, the baffle bolts are exposed to stresses caused by change in temperature and vibration. Over time, the stresses may fracture the bolt and weaken the integrity of the baffle assembly. To prevent damage to the baffle assembly, baffle bolts must be regularly inspected to ensure their integrity. Baffle bolt inspection may be performed underwater using ultrasonic testing.

Presently ultrasonic testing is performed by an X-Y-Z machine having an ultrasonic probe end effector fixed to the machine. The X-Y-Z machine comprises a dolly which may be positioned at any point around the periphery of the nuclear reactor pressure vessel. The dolly supports a hydraulicly controlled shaft which descends into the water where it can be moved vertically within the pressure vessel and horizontally toward or away from the baffle. Thus, the X-Y-Z machine provides three degrees of freedom. In use, the dolly is positioned outside the pressure vessel at a point corresponding to the baffle bolts location. The shaft is then lowered to the proper depth and the probe within the end effector is moved horizontally against the baffle bolt to be tested.

To properly perform an ultrasonic test of a baffle bolt, however, an ultrasonic probe must be delivered to the baffle bolt head and oriented so the probe assembly presses firmly and evenly to the baffle bolt head. This task is made more difficult due to the presence of the lock bar. To provide a continuous mating surface with the baffle bolt head, the ultrasonic testing probe must have a recess which receives a baffle bolt head lock bar. Because a baffle bolt head lock bar may be oriented in any direction, the ultrasonic probe must be rotatable so that the recess can be aligned with the lock bar. Unless the end effector is aligned exactly with the baffle bolt, a continuous mating surface will not be formed resulting in poor testing conditions. The X-Y-Z machine described above does not provide the necessary degrees of freedom to align the ultrasonic testing probe with the baffle bolt head. However, even if the X-Y-Z machine did have two extra degrees of freedom, the alignment procedure would likely be time consuming.

Those skilled in the art will realize that the operation performed by the X-Y-Z machine could be more efficiently performed by a robotic arm. Those skilled in the art will further realize that, extreme care must be taken to avoid contacting the robot arm, or an end effector thereon, with the baffle or the pressure vessel wall.

Therefore, there is a need for an end effector that floatably supports an ultrasonic testing device so that the testing device may be pressed flush against the baffle bolt head having a lock bar even if the end effector is not exactly aligned with the baffle bolt.

Further, there is a need for a robotic arm end effector which is releasably coupled to the wrist motor of a robotic arm to be used in a water filled nuclear reactor pressure vessels so that, should the end effector catch on the edge of the baffle, the portion of the end effector that is caught on the baffle will be released so that the robotic arm, end effector and baffle will not be damaged.

SUMMARY OF THE INVENTION

These and other needs are satisfied by the invention, which is directed to an end effector for a robotic arm which is operable inside a nuclear reactor pressure vessel. The end effector incorporates a releasable coupling between the end effector wrist motor and the operable end of the end effector. This invention is further directed to an ultrasonic probe testing device mounted floatably within an end effector, so that the probe may be brought into flush contact with a baffle bolt head having a lock bar even when the end effector is not exactly aligned with the baffle bolt.

A typical robot service arm is mounted above the cylindrical pressurized water vessel. The arm may be extended to or retracted from the periphery of the pressurized water vessel. Further, the arm is rotatable 360° so that it may be positioned above any point in the cylindrical vessel. The end of the robot arm may also travel vertically from the top of the vessel to the bottom. Thus, the arm by itself provides 3 degrees of freedom for the end effector. However, because the baffles are formed of flat plates, the baffle bolts may be as much as 90° perpendicular to the vessel wall. Accordingly, this invention provides an extra degree of freedom through a wrist assembly. Additionally, because the lock bar on the bolt head may be oriented in any direction, the mating surface of the ultrasonic testing probe must be rotatable to match the orientation of the lock bar. However, even with these two additional degrees of freedom, it would still be time consuming to precisely align the ultrasonic testing probe with the baffle bolt head.

Therefore, this invention provides a carriage which floatably supports an ultrasonic probe with a spring biasing the probe toward the front of the car In operation, the operator is not required to precisely align the probe with the baffle bolt to be tested. Once the probe is within plus or minus 2° of the baffle bolt to be tested, and the probe is oriented so that the groove on the probe mating surface is within plus or minus 2° of the baffle bolt lock bar, the operator then merely advances the probe into contact with the baffle bolt where upon the probe will adjust itself within the carriage so as to provide a constant interface between the probe and the baffle bolt.

A nuclear reactor pressure vessel baffle assembly has a saw-tooth pattern along its edges. Because the saw-tooth edge of the baffle has multiple corners, care must be taken when moving the robotic arm to ensure that the end effector does not catch on the saw-tooth edge. Without a release mechanism on the end effector, the end effector, the baffle, or both could be damaged if the end effector contacted the baffle during movement of the arm.

The invention provides for a vertically oriented wrist motor assembly which may be operated to rotate an ultrasonic probe assembly, or other device, in the horizontal plane. The ultrasonic probe assembly is releasably coupled to the wrist motor drive shaft so that, in the event of contact between the probe assembly and any structure, the entire assembly member is released from the wrist drive shaft so that it may spin freely thus preventing damage to the end effector or the other structure.

BRIEF DESCRIPTION OF THE DRAWINGS

A full understanding of the invention can be gained from the following description of the preferred embodiment when read in conjunction with the accompanying drawings in which.

DESCRIPTION OF THE PREFERRED EMBODIMENT

As used herein, the term "floatably" or "floatable" indicates a freedom to move, a small amount, in several directions while still being retained. That is, when directed to an ultrasonic probe floatably mounted in a housing, floatable indicates that the probe, while still being retained by the housing, has the freedom to roll, pitch, and yaw, as well as freedom to move laterally.

Figure 1:
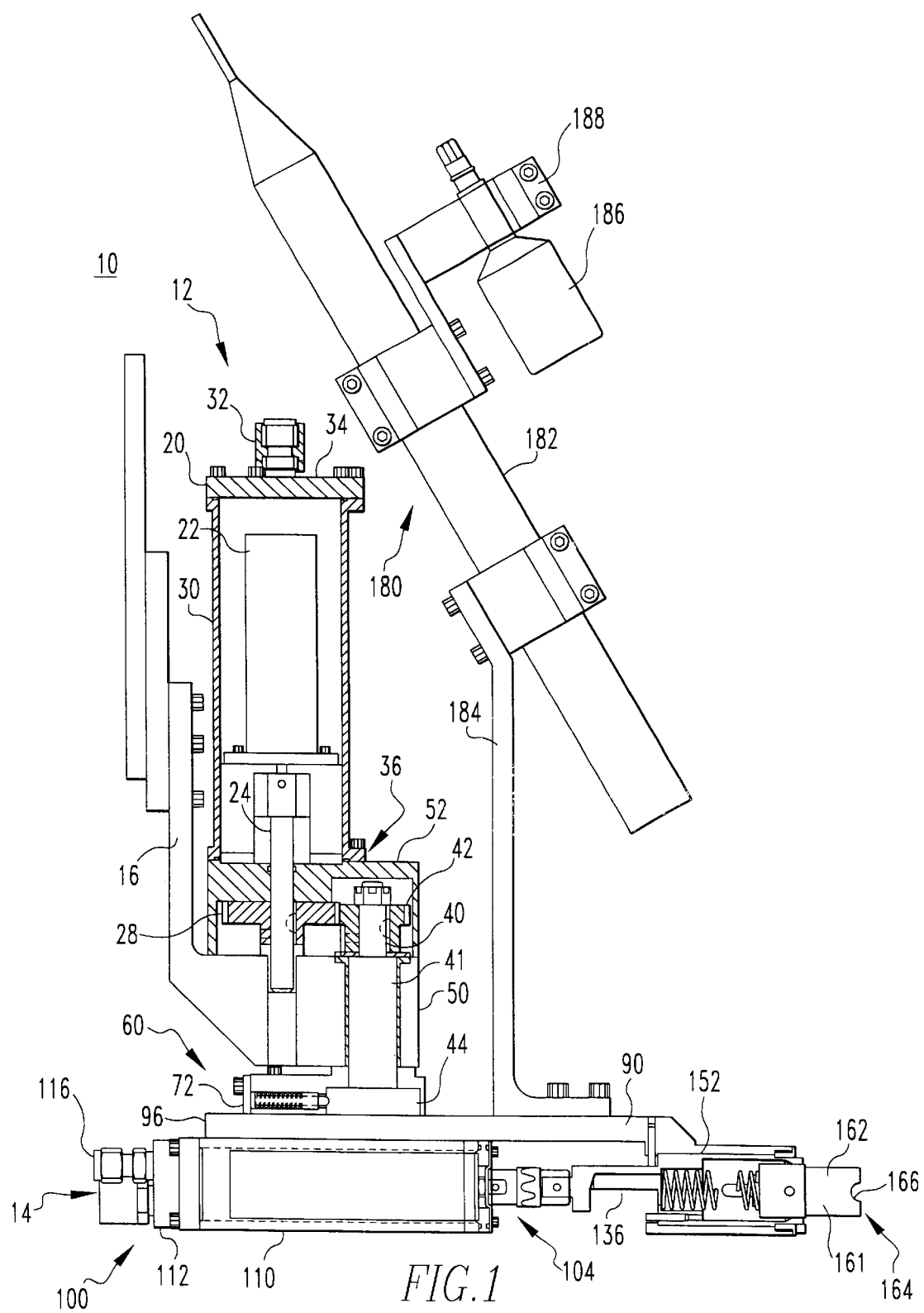
FIG. 1 is a partially fragmented view of the end effector.
Figure 2:
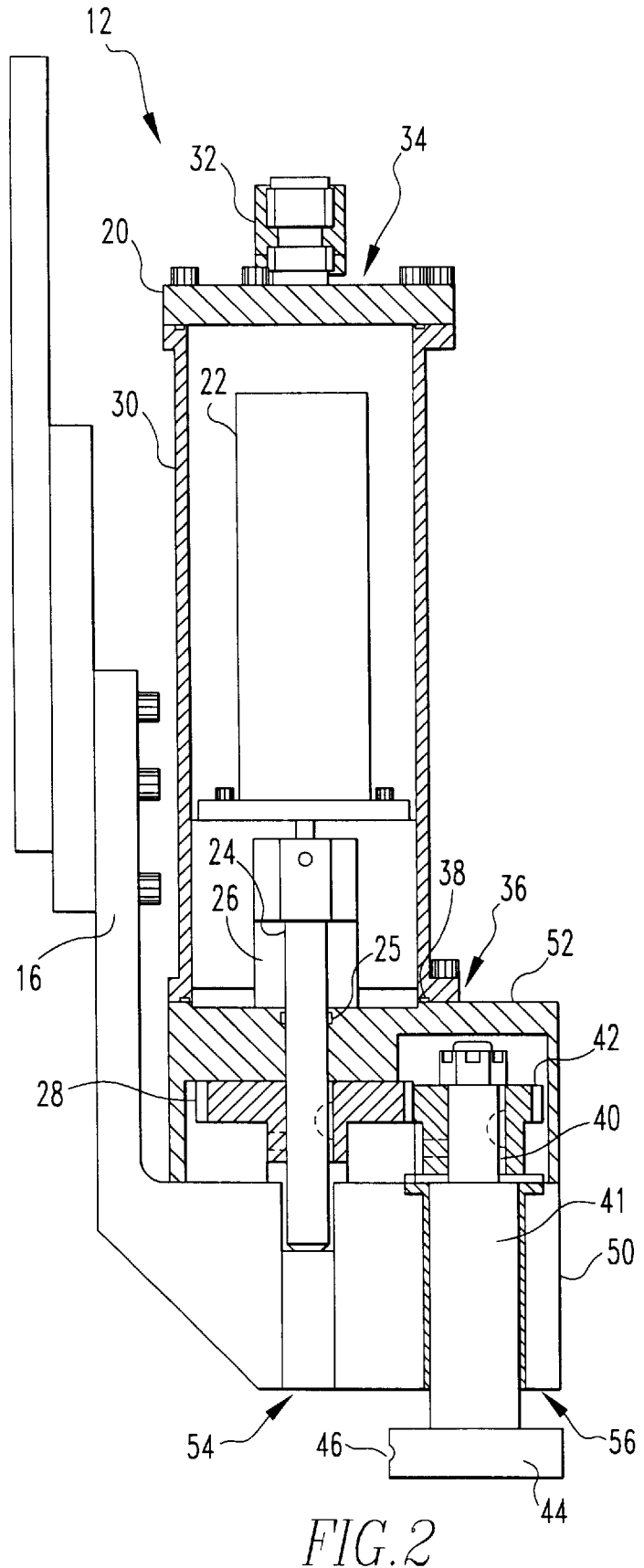
FIG. 2 is a partially fragmented view of wrist assembly.
Figure 3:
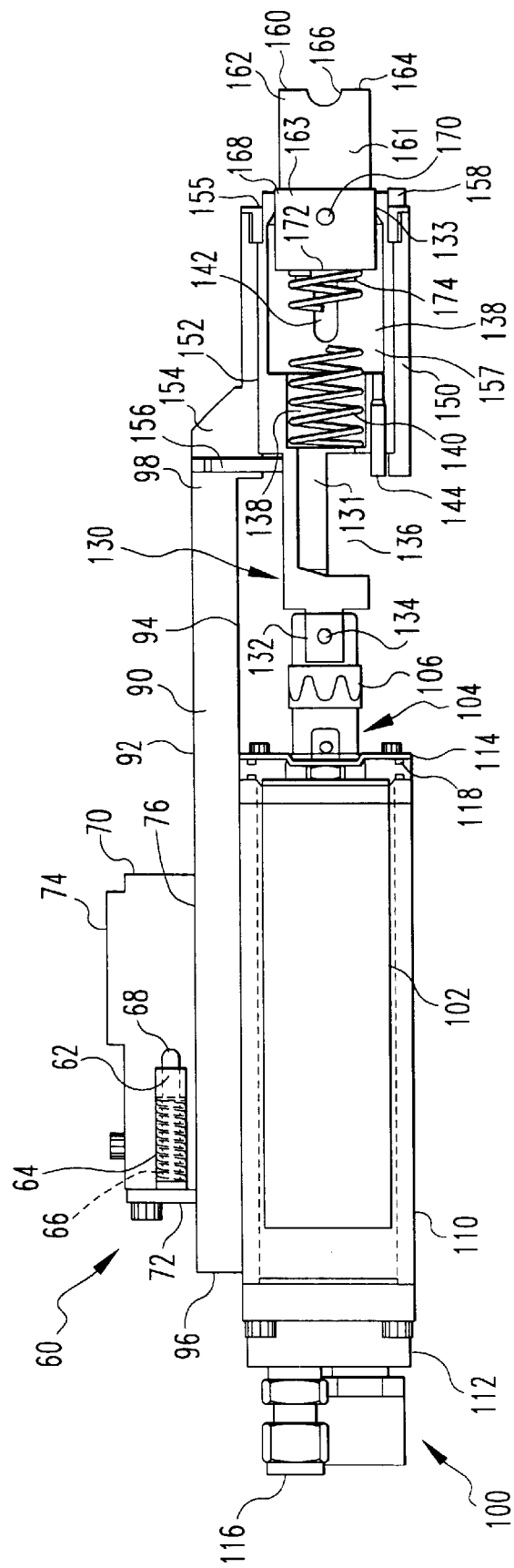
FIG. 3 is a partially fragmented view of the clutch assembly, probe motor, carriage assembly, and probe.

As shown in FIG. 1, an ultrasonic testing end effector 10 in accordance with the present invention is shown. The end effector is composed of two main components the wrist assembly 12 and a probe assembly 14. The wrist assembly 12, as shown in FIG. 2, includes the wrist motor assembly 20 and its housing 30, and the wrist shaft 40 and its housing 50. The probe assembly 14, as shown in FIG. 3, includes the clutch assembly 60 and its housing 70, a probe motor assembly 100 and its housing 110, a probe carriage assembly 130 and its housing 150, the probe 160, and camera assembly 180. Each of these assemblies will be described fully below. However, generally speaking, the probe assembly 14 rotates in a horizontal plane below the wrist assembly 12.

As shown in FIG. 2, the end effector 10 is coupled to a robotic arm by mounting bracket 16. Mounting bracket 16 supports the wrist motor assembly 20. The wrist motor assembly includes a wrist motor 22 which has a resolver 26 and a wrist axle 24 ending in a motor gear 28. The wrist motor 22, the upper portion of the wrist axle 24, and resolver 26 are enclosed within a wrist motor assembly housing 30. The wrist motor 22 can be any type of common motor that drives a rotating axle. The resolver 26 is a device which tracks the rotational motion of the wrist axle so that the angular orientation of the wrist axle 22 can be determined electronically by such means as a computer. The wrist motor assembly housing 30 has an upper surface 34 and a lower surface 36. The upper surface 34 has a medial hole therethrough (not shown). A wrist motor assembly coupling 32 is sealably connected to the upper surface 34 about the medial hole and provides a port which is coupleable to a power source and pressurized air hose. The coupling 32 also provides access for data wires connecting the resolver 26 to a computer or digital converter. The wrist motor assembly housing lower surface 36 has a medial hole therethrough which allows the lower portion of the wrist axle 24 to pass through.

The wrist axle 24 could be coupled with the clutch assembly 60 (described below) directly. In the preferred embodiment, however, the wrist axle motor gear 28 is rotatably coupled with a wrist shaft 40. The wrist shaft 40 is cylindrical and includes a wrist shaft body 41, a wrist gear 42 and a wrist shaft lower end 44. The wrist shaft lower end 44 may have a greater circumference than the wrist shaft body 41. The teeth of the wrist gear 42 are rotatably coupled with the teeth of the motor gear 28. The wrist shaft lower end 44 is generally circular except for a wrist shaft detent 46.

The motor gear 28, wrist shaft body 41 and wrist gear 42 are enclosed within the wrist shaft housing 50. The wrist shaft housing 50 has an upper end 52 and a lower end 54. Both the wrist shaft housing upper end 52 and the wrist shaft housing lower end 54 have openings therethrough. A wrist motor housing seal 38 is disposed between the wrist motor assembly housing 30 and the wrist shaft housing upper surface 52. The wrist motor housing seal provides a water tight seal between the wrist motor assembly housing 30 and the wrist shaft housing 50. The wrist motor assembly 20 is attached to the wrist shaft housing upper end 52 with the wrist axle 24 passing through the wrist shaft housing upper end 52 opening. A wrist axle seal 25 is disposed between the wrist shaft housing 50 and the wrist axle 24. The motor gear 28 is disposed at the lower end of the wrist axle 24 within the wrist shaft housing 50. The wrist shaft 40 is aligned in parallel with the wrist axle 24. The wrist shaft body 41 extends through the wrist shaft housing 50 and passes through the opening in the wrist shaft housing lower surface 54.

As shown in FIG. 3, a clutch pin assembly 60, which includes a clutch pin 62, a clutch pin housing 64, and a clutch pin spring 66, is enclosed within the clutch assembly housing 70. The clutch assembly housing includes a clutch assembly housing upper surface 74 with an opening therethrough, a clutch assembly housing lower surface 76 and a clutch assembly housing back plate 72. The clutch assembly housing upper surface 74 is rotatably connected to the wrist shaft housing lower surface 54. The wrist shaft housing lower surface 54 forms a bearing surface 56 at the point of contact between the wrist shaft housing lower surface 54 and the clutch assembly housing upper surface 74. The opening in the wrist shaft housing lower surface 54 and the opening in the clutch assembly housing upper surface 74 are aligned to allow the wrist shaft body 41 to pass from the wrist shaft housing 50 into the clutch assembly housing 70. The wrist shaft lower end 44 and wrist shaft detent 46 are disposed within the clutch assembly housing 70.

The clutch pin housing 64 extends from the clutch assembly housing back plate 72 towards the wrist shaft lower end 44. The clutch pin housing 64 contains the clutch pin spring 66 and the clutch pin 62. The clutch pin spring 66 biases the clutch pin 62 against the wrist shaft lower end 44. As shown in FIG. 1, when properly aligned, the clutch pin end 68 is disposed within the wrist shaft detent 46.

The clutch assembly housing 70 is attached to a frame 90. The frame 90 has a frame upper surface 92, a frame lower surface 94, a frame back end 96, and a frame front end 98. A carriage assembly motor assembly 100 is disposed below the frame back end 96. The carriage assembly motor assembly 100 includes a carriage assembly rotation motor 102, a carriage assembly axle 104 extending from the carriage assembly motor 102, a carriage assembly axle coupling 106 and a carriage assembly motor assembly housing 110. The carriage assembly rotation motor 102 is any common motor which can provide a rotational force to the carriage assembly axle 104. The carriage assembly motor assembly housing 110 is watertight and has a carriage assembly motor assembly housing back end 112, a carriage assembly motor assembly housing front end 114, a carriage assembly motor assembly housing coupling 116 and a carriage assembly motor assembly housing seal 118. The carriage assembly motor assembly housing back end 112 has an opening therethrough (not shown). The carriage assembly motor assembly housing coupling 116 is sealably connected to the carriage assembly motor assembly housing back end 112 about the medial hole. The carriage assembly motor assembly housing coupling 116 is coupleable to a power source and a positive pressure air tube. The carriage assembly axle 104 passes through an opening in the carriage assembly motor assembly housing front end 114. The carriage assembly motor assembly housing 110 is sealed from the external environment by the carriage assembly motor assembly housing seal 118, which is disposed annularly around the carriage assembly axle 104. The carriage assembly axle 104 terminates in a carriage assembly axle coupling 106.

Attached to, or integral to, the frame front end 98 is a probe carriage housing 150 which is a hollow cylindrical structure forming a probe carriage housing cavity 157. The internal surface of the probe carriage housing cavity 157 provides a bearing surface 152. The probe carriage housing further includes a back end 154 and a front end 155, both having openings therethrough connected to the probe carriage housing cavity. A probe carriage housing stop pin 156 is located adjacent to the probe carriage back end 154, and a probe carriage housing retainer 158 is located adjacent to the probe carriage front end 155.

The probe carriage assembly 130 is disposed within the probe carriage housing cavity 157 contacting the probe carriage housing bearing surface 152. The probe carriage assembly 130 is a hollow cylindrical body forming a probe carriage cavity 138 and having a coupling arm 131 extending therefrom. The probe carriage assembly coupling arm 131 terminates in a probe carriage coupling end 132 which is attached to the carriage assembly axle coupling 106 by a probe carriage coupling pin 134. The probe carriage assembly coupling arm 131 is offset from the center of the probe carriage assembly, so as to provide a probe carriage cord access notch 136. Along the inner surface 133 of probe carriage assembly 130 is a longitudinal probe carriage slot 142 having a length and a width. The probe carriage spring 140 and the probe 160 are disposed within the probe carriage cavity 138. The probe carriage spring 140 biases the probe 160 (described below) towards the front end of the probe carriage housing 155. The probe carriage assembly 130 is retained within the probe carriage housing 150 by the probe carriage housing retainer 158. The probe carriage assembly has at least one stop pin 144 extending from the probe carriage assembly back end 148.

The probe 160 includes a cylindrical probe body 161 having a front portion 162 and a back portion 163. The front portion 162 terminates in a circular mating surface 164. The mating surface 164 has a groove 166 thereon, which bisects the circular mating surface 164. The probe body back portion 163 is enclosed within an annular ring 168. The annular ring 168 has at least one external projection 170. When the probe 160 is disposed within the probe carriage assembly 130, the annular ring projection 170 is loosely fitted within the probe carriage slot 142. The probe carriage slot 142 and projection 170 limit the horizontal movement of the probe 160 within the probe carriage assembly 130, including limiting range of motion provided by the probe carriage spring 140. The projection 170, which is preferably circular, has a diameter that is smaller than the length and the width of the slot 142. Thus, the probe 160 has a limited range, preferably about 2 degrees, of yaw, pitch, and roll within the probe carriage assembly 130. The probe carriage back end 172 has a cylindrical disk 174 attached thereto. The cylindrical disk 174 provides a mating surface for the probe carriage spring 140. When the probe 160 is disposed within the probe carriage assembly 130, the probe carriage spring 140 biases the probe 160 towards the front end of the probe carriage housing.

Figure 4:
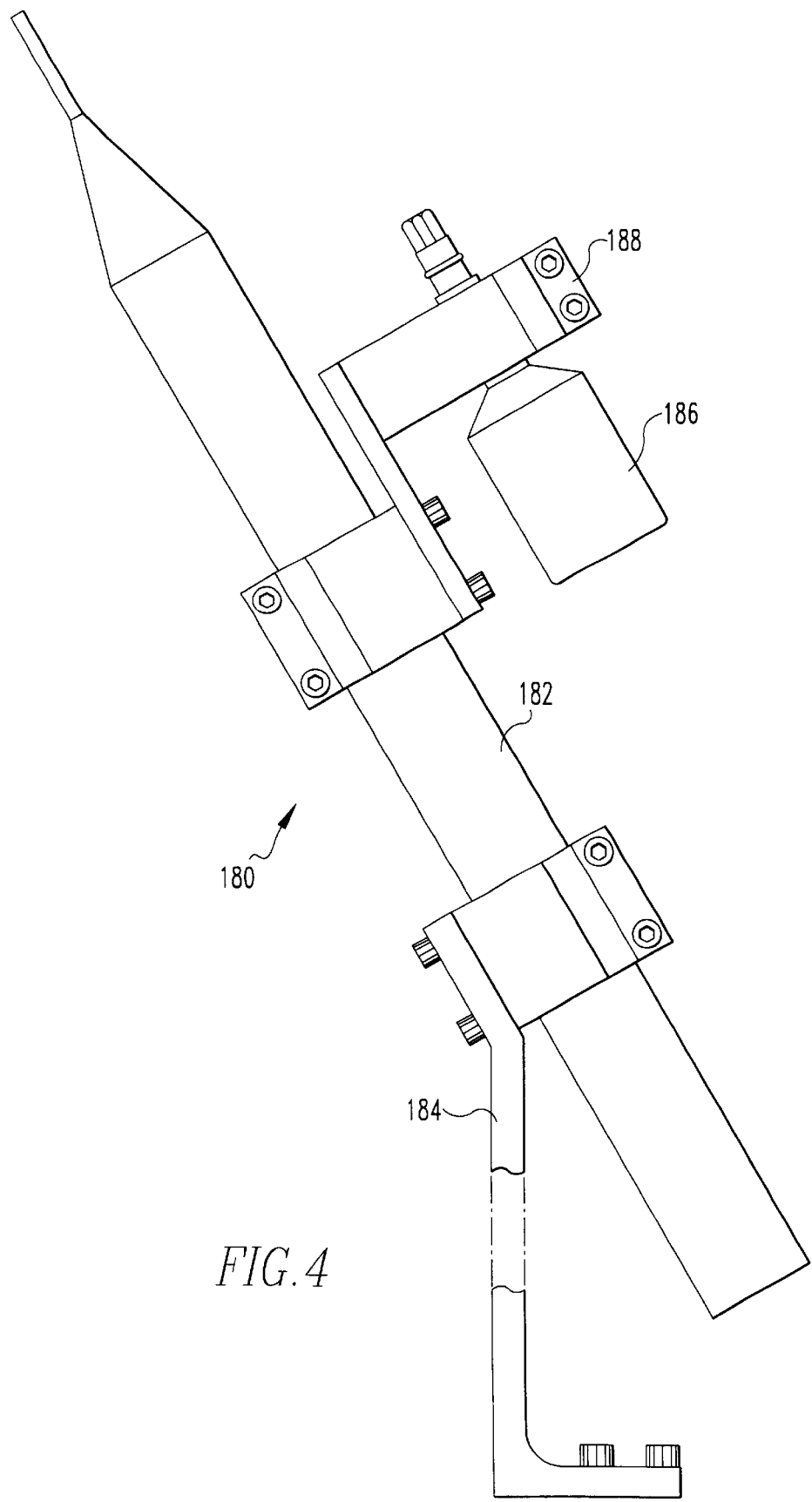
FIG. 4 is a lateral view of the camera and camera light.

As shown in FIGS. 1 and 4, in the preferred embodiment, a camera assembly 180 is attached to the frame upper surface 92 proximal to the frame front end 98. The camera assembly 180 includes a camera mounting bracket 184, a camera 182, a camera light mounting bracket 188, and a camera light 186. The camera mounting bracket 184 is attached to the frame 90 and provides support for the camera 182. The camera light mounting bracket 188, is attached to the camera 182 and provides support for the camera light 186. The camera 182 and the camera light 186 are oriented to point towards the probe 160. The camera 182 is connected by a cable (not shown) to a video display. The camera light 186 is connected by a power cord (not shown) to a power source.

Figure 5:
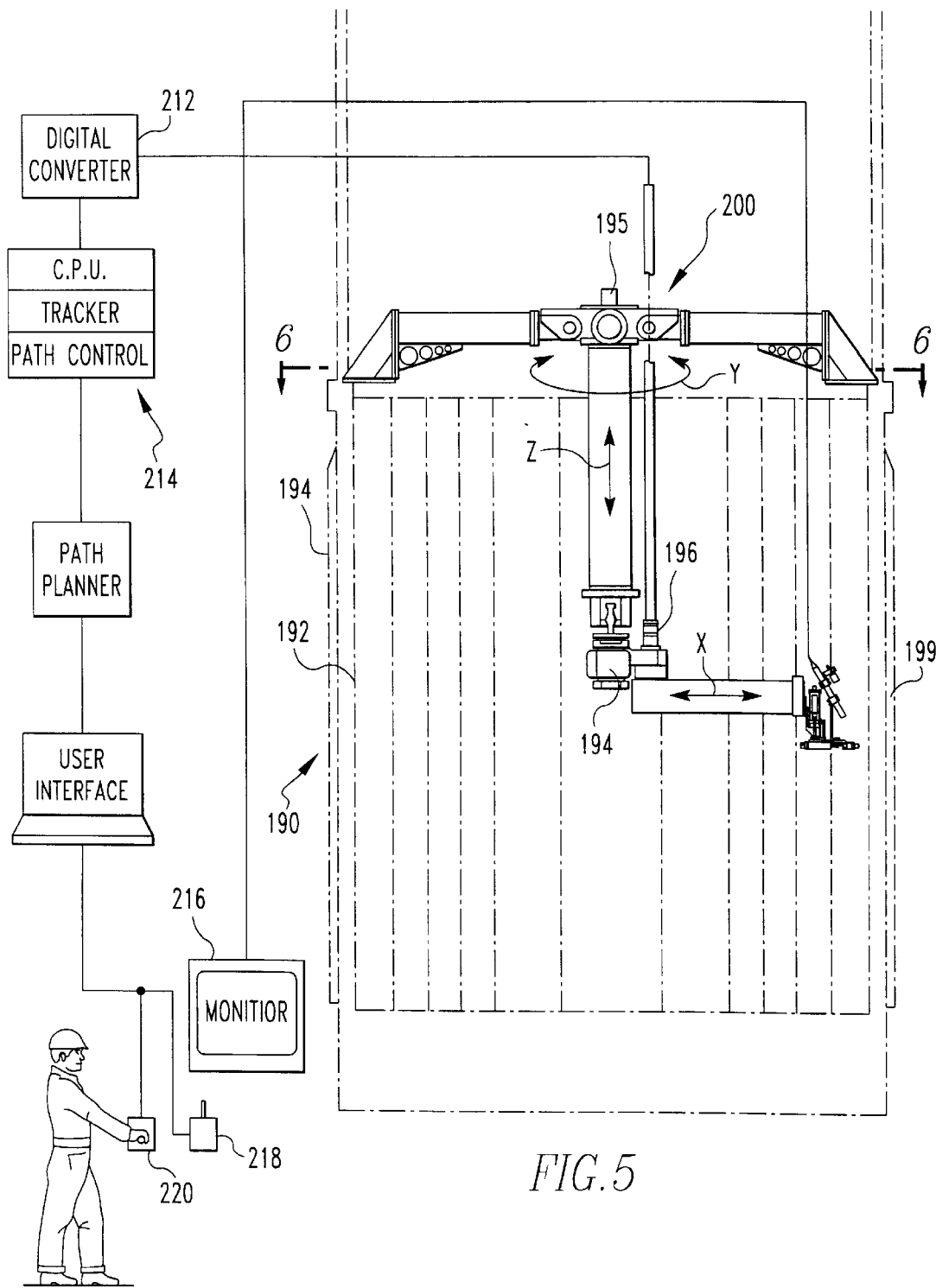
FIG. 5 is a view of a nuclear reactor pressure vessel and a schematic of the robotic arm controls.
Figure 6:
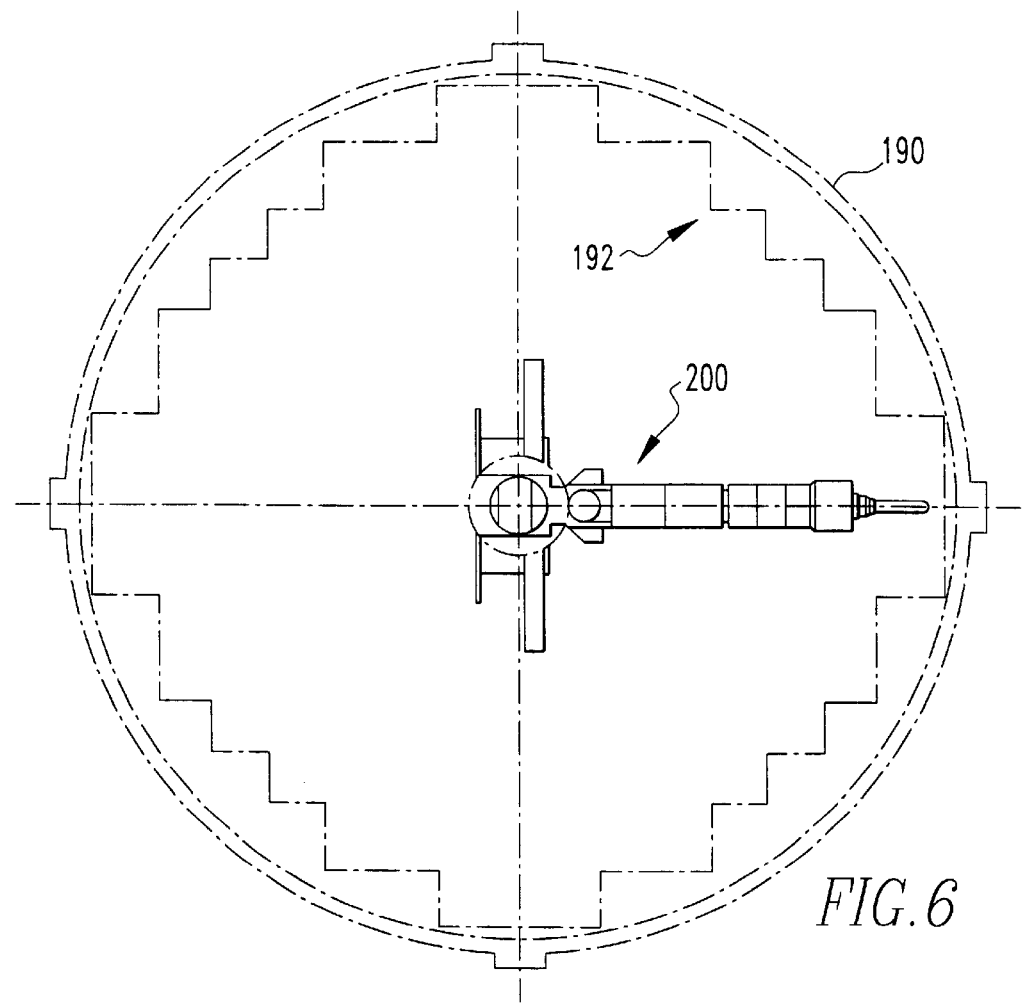
FIG. 6 is a view taken along line 6—6 on FIG. 5.
Figure 7:
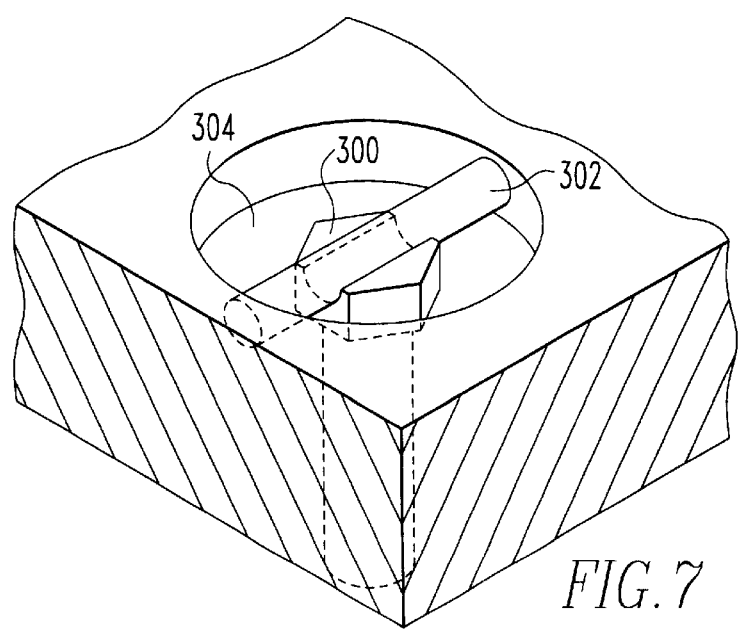
FIG. 7 is a perspective view of a baffle bolt and lock bar.

As shown in FIG. 5, a remotely operated service arm 200 ("ROSA" or "robot arm") is disposed above a cylindrical pressure vessel 190 for a nuclear reactor 190. As shown on FIGS. 5 and 6, within the cylindrical pressure vessel 190 is disposed a baffle 192 constructed of a plurality of flat plates forming a grid-like pattern. The baffle plates are secured to each other by baffle bolts along the outer periphery of the grid. As shown in FIG. 7, the baffle bolts 300 installed in recesses 304 on the baffle plates and locked into place by a lock bar 302 which is welded to the fastener head and the baffle 192.

The robot arm 200 is designed to position a variety of end effectors within the pressure vessel 190. As indicated by arrow X on FIG. 5, the robot arm moves toward or away from the pressure vessel wall 199 and, as indicated by arrow Y, the arm can rotate 360° about its axis, thus providing access to any point along the circumference of the pressure vessel. The robot arm is further designed to allow its end to travel vertically as indicated by arrow Z, substantially the entire length of the pressure vessel cylinder 190. Because the baffle bolts may be oriented perpendicular to the pressure vessel cylinder wall, the robot arm 200 must provide an additional degree of freedom in order to access the baffle bolt head. The ultrasonic testing end effector 10, and more specifically the wrist assembly 20, provides the additional degree of freedom required to inspect the baffle bolt heads. The ultrasonic testing end effector 10 is mounted on the robot arm 200, so that the wrist axle 24 rotates in a plane perpendicular to the robot arm's vertical plane of travel.

In operation, resolvers 194, 195, 196 on the robot arm 200 track the position of the end of the robot arm 200 and provide feedback to a digital converter 212. Using data from the resolvers and a computer controlled positioning system 214, the operator positions the end effector adjacent to the baffle bolt to be tested. Once in position, the camera 182 will display the baffle bolt on the operator's monitor 216. The operator then uses controls 218, 220, such as a joy-stick, to manually adjust the position of the mating surface of the probe 164 to be grossly aligned, within ±2 degrees of being perpendicular, with the baffle bolt. The operator then adjusts the orientation of the mounting surface groove 166 to be grossly aligned, within ±2 degrees, with the baffle bolt lock bar.

The mating surface 164 is then moved into contact with the baffle bolt. The mating surface 169 is biased against the baffle bolt by the force of the probe carriage spring 140. In the event of a slight misalignment between the baffle bolt and the mating surface 164, the probe 160 will correct its alignment to be flush due to the play provided by the loose fit between the probe carriage slot 142 and the projection 170. Once the mating surface 164 is flush with the baffle bolt, an ultrasonic test may be performed.

Once the test is complete, the end effector 10 can be moved to another baffle bolt. It is preferred to move the end effector either vertically or horizontally rather than diagonally. Because the baffle plates 192 run vertically, it is less likely that the end effector will catch on an edge while moving vertically. Conversely, given the proximity of the vessel wall to the sawtooth edge formed by the baffle plates, it is possible that the end effector will contact the baffle 192 during horizontal movement. Damage to the end effector 10 and the baffle 192 is prevented by the clutch assembly 60. In operation, the rotation of the wrist shaft 40 is translated to the clutch assembly 60 which is fixed to the frame member 90. The contact point between the wrist shaft 40 and the clutch assembly 60 is the clutch pin end 68 which is disposed within the wrist shaft detent 46. When the probe 160, carriage assembly 130 or the frame front end 98, contacts an immovable surface, such as a baffle plate 192, while the end effector 10 is being moved horizontally between baffle bolts, the clutch pin assembly 60, and all assemblies attached thereto will stop moving while the robot arm 200 and wrist motor assembly 20 continue to move. This action forces the clutch pin 62 to slide out of the wrist shaft detent 46 and contact the wrist shaft lower end 44. Because the wrist shaft lower end is cylindrical, there is little friction and the clutch pin assembly 60, and all assemblies attached thereto, will rotate freely about the wrist shaft lower end 44.

Both the wrist motor assembly housing 30 and the carriage assembly motor assembly housing 110 have couplings 32, 116 that provide access for pressurized air tubes. In operation the pressurized air tube create a positive pressure within the wrist motor assembly housing 30 and probe motor assembly housing 110 so that any seal leakage results in air escaping from the wrist motor assembly housing 30 or carriage assembly motor assembly housing 110 rather than water infiltration into the housing 30, 110.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

What is claimed is:

1. An end effector for supporting an ultrasonic testing probe on a robot arm having a robot mounting bracket, comprising:

a wrist assembly having a rotatable wrist shaft; said wrist assembly coupled to said robot mounting bracket;

a probe assembly rotatably coupled to said wrist shaft; said probe assembly structured to floatably support an ultrasonic testing probe having a body with a diameter and at least one projection; said probe assembly comprising:

a probe carriage assembly having a hollow cylindrical body and an interior surface; at least one longitudinal slot having a length and width on said interior surface; said interior surface having an interior diameter that is larger than said probe diameter;

said at least one projection disposed within said at least one slot; and said at least one projection having a smaller diameter than said length and width of said slot.

2. An end effector for supporting an ultrasonic testing probe within a nuclear reactor pressure vessel on a robot arm having a robot mounting bracket, comprising:

a wrist assembly having a rotatable wrist shaft; said wrist assembly coupled to said robot mounting bracket;

a probe assembly rotatably coupled to said wrist shaft; said probe assembly structured to floatably support an ultrasonic testing probe having a body with a diameter and at least one projection; said probe assembly comprising:

a probe carriage assembly having a hollow cylindrical body and an interior surface; at least one longitudinal slot having a length and width on said interior surface; said interior surface having an interior diameter that is larger than said probe diameter;

said at least one projection disposed within said at least one slot; and said at least one projection having a smaller diameter than said length and width of said slot.

3. The end effector of claim 2 wherein said probe has a body having a cross-sectional area and said carriage assembly hollow body has a cross-sectional area that is larger than the probe cross-sectional area.

4. The end effector of claim 3 wherein said probe carriage assembly has a front end; and further includes a means disposed within said probe carriage assembly structured to bias a probe toward said front end of said carriage assembly.

5. The end effector of claim 2 wherein said probe carriage assembly has a front end, and further includes a spring disposed within said carriage assembly structured to bias a probe toward said front end of said carriage assembly.

6. The end effector of claim 5 wherein said probe assembly includes a camera assembly disposed above said probe assembly.

7. The end effector of claim 5, wherein said probe carriage assembly is rotatable about a longitudinal axis.

8. The end effector of claim 7 wherein said probe assembly further includes:

a frame member coupled to said wrist shaft;

said frame member having a front end and a back end;

a hollow cylindrical probe carriage housing integral to said frame member front end;

said probe carriage assembly rotatably disposed within said probe carriage housing.

9. The end effector of claim 8, wherein said probe assembly includes:

a pin extending from said probe carriage housing adjacent to said probe carriage back end;

said probe carriage assembly having a back end with at least one stop pin extending therefrom;

during rotation of said probe carriage assembly, said at least one stop pin contacts said probe carriage housing pin limiting rotation of said probe carriage assembly to less than 360° within said probe carriage housing.

10. The end effector of claim 7, wherein said probe assembly includes a carriage assembly rotation motor coupled to said probe carriage assembly.

11. The end effector of claim 10, wherein said probe carriage assembly has a back end coupling arm extending therefrom;

said coupling arm attached to said carriage assembly rotation motor.

12. The end effector of claim 11, wherein said coupling arm has a notch to provide access for cables connected to a probe disposed within said probe assembly.

13. The end effector of claim 12 wherein said probe assembly further includes:

a frame member coupled to said wrist shaft;

said frame member having a front end and a back end;

a hollow cylindrical probe carriage housing integral to said frame member front end;

said probe carriage assembly rotatably disposed within said probe carriage housing.

14. The end effector of claim 13, wherein said probe assembly includes:

a pin extending from said probe carriage housing adjacent to said probe carriage back end;

said probe carriage assembly including at least one stop pin extending from said probe carriage back end;

during rotation of said probe carriage assembly, said at least one stop pin contacts said probe carriage housing pin limiting rotation of said probe carriage assembly to less than 360° within said probe carriage housing.

15. The end effector of claim 14, wherein said probe assembly and a camera assembly is disposed above said probe assembly.

16. An end effector for supporting an ultrasonic testing probe on a robot arm having a robot mounting bracket, comprising:

a wrist assembly having a rotatable wrist shaft; said wrist assembly coupled to said robot mounting bracket;

a probe assembly rotatably coupled to said wrist shaft, including a clutch assembly releasably coupling said probe assembly to said wrist shaft wherein said clutch assembly comprises:

a clutch pin;

said wrist shaft having a lower end and said lower end having a detent; and a means to bias said clutch pin against said lower end detent;

said probe assembly structured to floatably support an ultrasonic testing probe.

17. The end effector of claim 16 wherein said clutch assembly further includes:

a clutch assembly housing having a back plate;

said clutch assembly housing being rotatably attached to said wrist assembly and fixedly attached to said probe assembly;

clutch pin housing;

a clutch pin spring;

said shaft lower end disposed within said clutch assembly housing;

said clutch pin housing fixedly attached to said clutch assembly housing back plate;

said clutch pin spring and said clutch pin disposed within said clutch pin housing;

said clutch pin spring biasing said clutch pin against said lower end detent.

18. The end effector of claim 17 wherein said wrist assembly comprises:

a wrist motor;

a resolver integral to said wrist motor;

a mounting bracket attached to said wrist motor and coupled with said robot mounting bracket.

19. The end effector of claim 18, wherein said probe assembly includes a camera assembly attached to said frame member.

20. A method of ultrasonically inspecting a bolt, comprising the steps of:

positioning a robotic arm end effector adjacent to a bolt head having a lock bar, said end effector having wrist assembly which supports a probe assembly, said probe assembly floatably supporting an ultrasonic probe and biasing said probe toward said bolt head, said probe having a mating surface with a groove;

rotating said wrist in a first plane to grossly align said ultrasonic probe with said bolt head;

rotating said ultrasonic probe in a second plane to grossly align said groove with said lock bar;

bringing said ultrasonic probe into contact with said bolt head;

allowing floatable probe to align flush with said bolt head; and performing ultrasonic testing.

21. The method of claim 20 wherein said robotic arm has a camera assembly to provide visual feedback to aid in aligning said ultrasonic probe with said bolt head and lock bar, and wherein said gross alignment is performed using visual feed back.

* * * * *